(12) United States Patent
Berry et al.

(10) Patent No.: US 8,908,943 B2
(45) Date of Patent: Dec. 9, 2014

(54) PERSONALIZED ANATOMICAL DIAGNOSTICS AND SIMULATIONS

(75) Inventors: Matthew M. Berry, Highland, UT (US); Robert M. Berry, Highland, UT (US); Daniel D. Lyman, Provo, UT (US)

(73) Assignee: Orca Health, Inc., Sandy, UT (US)

( * ) Notice: Subject to any disclaimer, the term of this patent is extended or adjusted under 35 U.S.C. 154(b) by 302 days.

(21) Appl. No.: 13/477,794

(22) Filed: May 22, 2012

(65) Prior Publication Data
US 2013/0315452 A1     Nov. 28, 2013

(51) Int. Cl.
  *G06K 9/00*  (2006.01)
  *G06F 19/00*  (2011.01)
(52) U.S. Cl.
  CPC .......... *G06F 19/3406* (2013.01); *G06F 19/322* (2013.01)
  USPC ......................................................... 382/128
(58) Field of Classification Search
  None
  See application file for complete search history.

(56) References Cited

U.S. PATENT DOCUMENTS

| | | | |
|---|---|---|---|
| 5,748,907 A | 5/1998 | Crane | |
| 5,766,016 A | 6/1998 | Sinclair et al. | |
| 5,924,074 A * | 7/1999 | Evans | 705/3 |
| 6,383,135 B1 | 5/2002 | Chikovani et al. | |
| 7,107,547 B2 | 9/2006 | Cule et al. | |
| 7,962,348 B2 * | 6/2011 | Dew et al. | 705/2 |
| 2002/0082865 A1 | 6/2002 | Bianco et al. | |
| 2003/0208324 A1 | 11/2003 | Bellwood et al. | |
| 2005/0104896 A1 | 5/2005 | Kerr | |
| 2007/0236514 A1 | 10/2007 | Agusanto et al. | |
| 2007/0242069 A1 | 10/2007 | Matsue | |
| 2008/0027917 A1 | 1/2008 | Mukherjee | |
| 2008/0136838 A1 | 6/2008 | Goede et al. | |
| 2008/0177602 A1 | 7/2008 | Sopher et al. | |
| 2008/0242953 A1 * | 10/2008 | Dew et al. | 600/300 |
| 2010/0070297 A1 | 3/2010 | Kharraz Tavakol et al. | |
| 2010/0070300 A1 | 3/2010 | Anderson et al. | |
| 2010/0257214 A1 * | 10/2010 | Bessette | 707/812 |
| 2010/0287001 A1 | 11/2010 | Pearce et al. | |
| 2011/0145693 A1 | 6/2011 | Mutic | |
| 2011/0170752 A1 * | 7/2011 | Martin et al. | 382/128 |
| 2011/0264503 A1 | 10/2011 | Lenahan et al. | |
| 2012/0159391 A1 | 6/2012 | Berry et al. | |
| 2012/0206694 A1 | 8/2012 | Raskar | |
| 2012/0280988 A1 | 11/2012 | Lampotang et al. | |
| 2013/0071827 A1 | 3/2013 | Berry et al. | |
| 2013/0211284 A1 | 8/2013 | Berry et al. | |
| 2013/0315452 A1 * | 11/2013 | Berry et al. | 382/128 |

(Continued)

OTHER PUBLICATIONS

Biggs, John, Up Close With Biodigital's 3D Human Simulator [TCTV], TCTechCrunch, Apr. 25, 2012, http://techcrunch.com/2012/04/25/up-close-with-biodigitals-3d-human-simulator-tctv/.

(Continued)

*Primary Examiner* — Tahmina Ansari
(74) *Attorney, Agent, or Firm* — Workman Nydegger

(57) ABSTRACT

Interfaces and other systems are provided to receive input corresponding to anatomical elements. The anatomical elements are rendered on the interfaces or other systems with visual, audio and/or haptic feedback. Simulations of the anatomical elements can reflect the impact of existing and anticipated conditions. Personalized conditions and other data can also be used to modify and personalize the simulations and other output. Various controls are provided by the interfaces and systems to access and modify settings associated with personalized and generalized condition input data. Some simulations incorporate real-time data to mimic personalized anatomical elements.

19 Claims, 11 Drawing Sheets

(56) References Cited

U.S. PATENT DOCUMENTS

| | | |
|---|---|---|
| 2014/0022283 A1 | 1/2014 | Chan et al. |
| 2014/0122096 A1 | 5/2014 | Berry et al. |
| 2014/0204118 A1 | 7/2014 | Berry et al. |
| 2014/0215370 A1 | 7/2014 | Berry |

OTHER PUBLICATIONS

U.S. Appl. No. 14/477,540, filed Sep. 4, 2014, Berry et al.
U.S. Appl. No. 14/251,400, filed Apr. 11, 2014, Mainwaring et al.
U.S. Appl. No. 62/045,968, filed Sep. 4, 2014, Mainwaring et al.
VueCare Media, Vue Simulator, Demo video accessed at: http://www.vuecaremedia.com/vuesim_demo.html, copyright 2010.
VueCare Media, Vue Simulator, About page accessed at: http://web.archive.org/seb/20110207031345/http://vuecaremedia.com/vuesim.html, available at least as early as Feb. 7, 2011.
VueCare Media: The Eye Channel Network press release accessed at: http://vuecaremedia.com/Final%20Press%20Release%2011-1-10.pdf, Created Dec. 23, 2010.
Pivi & Co, FatBooth, http://itues.apple.com/us/app/fatbooth/id372268904?mt=8, Available at least as early as Dec. 19, 2012, Version 3.4.
Welcome to the AR Lungs Website, http://www.arlungs.com/, Available at least as early as Jan. 7, 2013.
Mirracle, http://mirracle.de/, First Prototype of Magic Mirror, Jan. 3, 2011.
U.S. Appl. No. 13/093,272, Dec. 4, 2013, Office Action.
U.S. Appl. No. 13/093,272, May 16, 2014, Notice of Allowance.
U.S. Appl. No. 12/237,530, Feb. 1, 2013, Preinterview First Office Action.
U.S. Appl. No. 13/237,530, Apr. 19, 2013, Office Action.
U.S. Appl. No. 13/237,530, Oct. 1, 2013, Office Action.
U.S. Appl. No. 13/237,530, Mar. 20, 2014, Office Action.
U.S. Appl. No. 13/838,865, Nov. 18, 2013, Office Action.
U.S. Appl. No. 13/838,865, May 15, 2014, Office Action.
U.S. Appl. No. 13/663,820, Jun. 6, 2013, Office Action.
U.S. Appl. No. 13/663,820, Oct. 2, 2014, Office Action.
U.S. Appl. No. 13/747,595, Oct. 8, 2014, Office Action.

\* cited by examiner

PERSONALIZED ANATOMICAL DIAGNOSTICS AND SIMULATIONS

BACKGROUND OF THE INVENTION

1. The Field of the Invention

This invention relates to systems, methods, and computer program products which can be used to facilitate diagnosis and simulations of living organisms, including computing interfaces and devices capable of rendering anatomical elements and relevant information for related conditions and treatment options.

2. The Relevant Technology

Modern medical practices and information technologies have enriched and extended human life by identifying and disseminating medical information which can help individuals pursue healthy life choices and that is usable to treat a variety of medical conditions.

The application of appropriate medical treatments is often dependent upon the accuracy of medical diagnosis as well as the education that medical practitioners and patients have regarding any particular medical condition and the corresponding consequences of different treatment options.

Computing technologies can facilitate the foregoing education of medical practitioners and patients. For instance, some computing systems have been developed that are capable of identifying and rendering specific anatomy and for diagnosing and providing information related to the treatment options for particular anatomical conditions. It is now commonplace in the medical profession to see the use of multimedia systems to at least supplement the education of medical practitioners, as well as patients, regarding anatomical conditions and related treatments.

Unfortunately, the variety and complexities of biological anatomy make it difficult to present any single system or interface that is capable of accommodating the educational needs and preferences of all medical practitioners and patients. Existing interfaces and educational materials, for example, are typically generalized and fail to provide the level of personalization that is typically desired and sometimes necessary to adequately educate a patient or medical professional regarding a particular patient's anatomy, diagnosis, and/or available treatment options.

Accordingly, there remains an ongoing need for further development in the field of medicine, with particular regard to the manner in which computing systems are used for identifying and presenting information related to different anatomical conditions and treatment options.

BRIEF SUMMARY OF THE INVENTION

The present invention is generally related to methods, systems and computing interfaces which are capable of being used to identify and render anatomical presentations and other information related to anatomical conditions and treatment options.

According to one embodiment, a computing interface provides video, audio and/or haptic feedback for rendering anatomical presentations. The computing interface also provides controls for modifying the presentation of the rendered anatomical elements. The anatomical elements are simulated with varying degrees of richness, by displaying different layers, granularities, details, annotations, animations, visual characteristics, audio characteristics, haptic feedback and/or other customizations, to thereby accommodate different educational needs and preferences.

In some embodiments, anatomical elements are displayed intact. In other embodiments, one or more portions of the anatomical elements are deconstructed and displayed in a sliced format, an exploded format, or other deconstructed format.

Related medical information for a particular individual can also be provided to customize the display of the anatomical elements by modifying the elements in such a way as to reflect personalized medical information. This medical information can be provided by the user, a medical professional, a third party provider or a sensory or other type of computing system.

In some embodiments, real-time data is received and used to modify the display or other simulation of the rendered anatomical elements, dynamically and on-the-fly.

Anatomical conditions and treatment information related to the displayed anatomical elements can also be presented to the user, to thereby facilitate understanding and treatment.

In some embodiments, animations are used to demonstrably reflect the anticipated effect of a condition or treatment on the displayed anatomical elements over time. Other animations are used to reflect personalized real-time data for existing conditions experienced by the rendered anatomical elements.

Information associated with the rendered anatomical elements and conditions is also shared, in some instances, with medical practitioners and other caregivers to facilitate awareness of emergency conditions and to expedite possible treatments.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
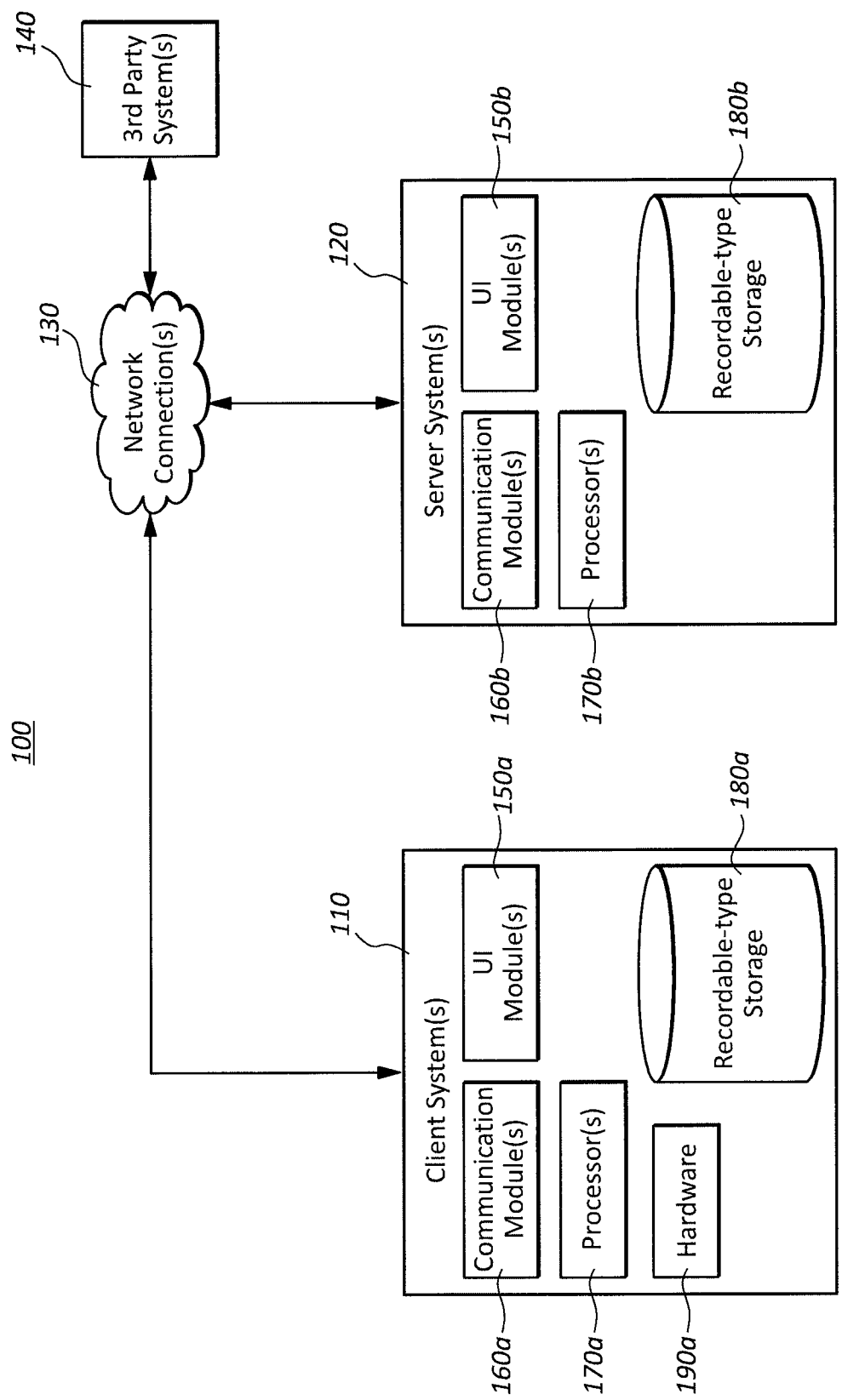
FIG. 1 illustrates one example of a computing environment that can be used to practice, and which can incorporate, aspects of the invention.

Computing interfaces are utilized by the present invention for facilitating education and communication throughout the medical community. These interfaces are capable of simulating the impact of various conditions and treatments on different anatomical elements. The interfaces are also capable of being used to facilitate communication between medical practitioners and patients.

In some embodiments, mobile devices such as tablets, mobile phones or smart devices are utilized to access the inventive user interfaces. In addition to the foregoing types of mobile devices, the concepts of the invention are implemented in other mobile devices as well, those other mobile devices comprising any wireless, hand-held, or portable devices. In other embodiments, desktop computers, servers, kiosks, gaming systems and/or other devices, which are not necessarily considered mobile, are used.

Preferably, although not necessarily, the consumer devices include or are communicably coupled with touch screens, such as on a tablet computing device, capable of receiving user input and displaying relevant output/feedback. In other embodiments, keyboards, rollers, touch pads, sticks, mice, microphones and/or other input devices are used to receive input. Speakers, printers and display screens, which are not touch sensitive, as well as oscillators, vibrating devices and other tactile feedback devices, are used to render corresponding output.

User interfaces are utilized to render anatomical elements, such as the heart shown in FIGS. 2-10, along with user interface controls that are operable and selectively used to manipulate and explore information related to the displayed anatomical elements.

As described herein, the term "anatomical element(s)" broadly refers to any anatomical organ, system, assembly, subassembly, structure, object or any combination thereof. While much of the following disclosure, particularly with regard to FIGS. 2-10, describes aspects of the invention with regard to displayed organs comprising hearts, it will be appreciated that the invention equally applies to the rendering of other organs, such as lungs, livers, brains, or other organs, as well as other anatomical elements, such as, but not limited to, optical, neurological, muscular, skeletal, lymphatic, cardiovascular, pulmonary, chemical, and/or other anatomical elements of both human or other biological forms. At times, the term "anatomical element(s)" is used interchangeably herein with the term "anatomical structure" or "anatomical object."

Some types of anatomical elements that can be rendered and techniques and systems that are capable of rendering anatomical elements are described in one or more of the following applications: U.S. patent application Ser. No. 13/093,272, filed on Apr. 25, 2011, entitled "Medical Interface Annotation and Communication Systems"; U.S. patent application Ser. No. 13/167,600, filed on Jun. 23, 2011, entitled "Interactive Medical Diagnosing with Portable Consumer Devices"; U.S. patent application Ser. No. 13/167,610, filed on Jun. 23, 2011, entitled "Using Mobile Consumer Devices to Communicate with Consumer Medical Devices"; and U.S. patent application Ser. No. 13/237,530, filed on Sep. 20, 2011, entitled "Interactive and Educational Vision Interfaces." Each of the foregoing applications is incorporated herein by reference in its entirety. Accordingly, aspects of this invention include any combination of the concepts described in this disclosure as well as the concepts presented with the disclosures of the foregoing applications.

Computing Environment(s)

Embodiments of the present invention may comprise or utilize special purpose or general-purpose computing devices that include computer hardware, such as, for example, one or more processors and system memory, as discussed in greater detail below. Embodiments within the scope of the present invention also include physical and other computer-readable and recordable-type media for storing computer-executable instructions and/or data structures. Such computer-readable and recordable media can be any available media that can be accessed by a general purpose or special purpose computer system. Computer-readable media that store computer-executable instructions according to the invention are recordable-type storage media or other physical computer storage media (devices) that are distinguished from merely transitory carrier waves.

Computer-readable media that carry computer-executable instructions are transmission media. Thus, by way of example, and not limitation, embodiments of the invention can comprise at least two distinctly different kinds of computer-readable media: computer storage media (devices) and transmission media.

Computer storage media (devices) includes RAM, ROM, EEPROM, CD-ROM, DVD-ROM, HD-DVD, BLU-RAY or other optical disk storage, magnetic disk storage or other magnetic storage devices, or any other medium which can be used to store desired program code means in the form of computer-executable instructions or data structures and which can be accessed by a general purpose or special purpose computer and which are recorded on one or more recordable-type medium (device).

A "network" and "network connection(s)," as defined herein, include one or more data links or communication channels that enable the transport of electronic data between computer systems and/or modules and/or other electronic devices. When information is transferred or provided over a network or another communications connection or channel (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions comprise, for example, software instructions and data which, when executed at one or more processor, cause one or more general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described herein. Rather, the described features and acts are disclosed as example forms of implementing the claims.

Those skilled in the art will appreciate that the invention may be practiced in network computing environments with many types of computer system configurations, including personal computers, desktop computers, laptop/notebook computers, message processors, hand-held devices, multiprocessor systems, microprocessor-based or programmable consumer electronics, network PCs, minicomputers, mainframe computers, tablets, mobile telephones, wireless or other mobile devices, electronic toys, exercise equipment, portable computing devices, PDAs, pagers, routers, switches, and the like, and combinations of the foregoing.

The invention may also be practiced in distributed and cloud system environments where local and remote computer systems, which are linked (either by hardwired data links, wireless data links, or by a combination of hardwired and wireless data links) through a network, all perform tasks. In a distributed system environment, program modules may be located in both local and remote memory storage devices.

FIG. 1

FIG. 1 illustrates an exemplary computing environment 100 that incorporates various systems of the invention. These systems are used to implement methods of the invention and are capable of generating, accessing and rendering user interfaces of the invention to facilitate the presentation of and interactivity with rendered anatomical elements, as well as other information.

The illustrated computing environment 100 includes one or more client systems 110 in communication with one or more server systems 120 through one or more network connections 130. The network connections 130 can include any combination of Local Area Network ("LAN") or Wide Area Network ("WAN") connections, including the Internet and one or more proxy servers. These connections can also include wired and/or wireless communication channels.

The client and server systems 110, 120 are also shown to be in communication with one or more third party systems 140 through network connections 130. Each of these systems can comprise standalone systems (as generally shown) or, alternatively, distributed systems.

As illustrated, the client and server systems 110, 120 are each configured with a plurality of user interface modules 150a, 150b and communication modules 160a, 160b of computer-executable instructions and data structures which, when executed by one or more processors 170a, 170b of the client and server systems 110, 120, implement aspects of the invention.

The communication modules 160a, 160b, for example, when executed by one or more processors 170a, 170b, are operable to facilitate wireless and/or wired communications through the network connections 130. Any data can be included in these communications, including image data, sound data, and character or text data. The communication modules are also configured to encrypt and decrypt data and to perform authentication of user and system credentials.

The interface modules 150a, 150b include computer-executable instructions that, when executed by the one or more processors 170a, 170b, are operable to render the user interfaces described herein.

The client and server systems 110, 120 also include recordable-type storage 180a, 180b, such as, but not limited to system memory or portable storage devices. This storage 180a, 180b can be configured to store any type and quantity of different data, including the interfaces described herein, as well as the various modules described above, as well as medical information and records (both public and personal/confidential records). It will also be appreciated that the storage 180a, 180b can also be distributed among a plurality of different devices or systems, including the third party systems 140, and does not necessarily need to be constrained to a single physical device. In some embodiments, however, the storage 180a and/or 180b are constrained to a single device.

In some embodiments, each of the illustrated client system(s) 110, server system(s) 120 and/or third party systems 140 comprises a mobile device. Such a mobile device can include any wireless device, such as, but not limited to, a cell phone, a tablet computer, a notebook computer, a PDA, and/or any other type of smart device. The mobile device can also comprise other types of mobile devices. Preferably, although not necessarily, the mobile device will have an integrated display screen and/or speakers or other output devices that are included within the hardware 190a of the mobile device and that are capable of rendering image data, audio data, and/or tactile data to a user via the interface modules 150a and/or 150b, for example. In other embodiments, the mobile device is equipped with drivers and connectors that are operable to connect the mobile device to auxiliary display screens, speakers devices and/or tactile output devices. In some embodiments, the hardware 190a of the client system 110 includes a touch-sensitive screen capable of receiving touch input at the display screen of the client system 110, such as, for example, when the touch-sensitive screen is touched.

In some alternative embodiments, the mobile device does not include a display screen, but implements aspects of the invention, by outputting tactile and/or audio output through an appropriate and corresponding tactile output device (e.g., haptic output device) or audio output device. These types of devices, by way of no-limiting example, can include portable speakers, exercise monitors and equipment, and electronic toys. These devices can also include auxiliary devices that are wirelessly coupled to the client systems or that are coupled through a wired connection to the client systems. These coupled devices can, therefore, be considered as part of the client systems or as independent systems.

It will be appreciated that display and audio hardware 190a of the client system 110 and corresponding hardware on third party systems 140 can be particularly useful during implementation of various embodiments described herein to enable medical professionals and users to remotely interface via video conferencing or teleconferencing.

Each of the systems shown, including the server system 120 and third party systems 140 include hardware, storage, and software components useful for implementing the functionality of the invention, and can include, therefore, any of the hardware and software components described throughout this disclosure or that would be understood by one of skill in the art as being capable of implementing the described functionality of the claimed invention. In this regard, it will be appreciated that the server system 120 and $3^{rd}$ party system(s) 140 also includes various hardware, although not shown, similar to or the same as the hardware 190a of client system 110.

In some embodiments, the third party system(s) 140 include portable consumer devices, such as medical aids (e.g., hearing aids, pace makers, insulin devices, prosthetic devices, and so forth), sensory devices (e.g., heart rate monitors, neurological sensors, temperature sensors, moisture sensors, pressure sensors, and so forth), exercise equipment (e.g., treadmills, bikes, elliptical machines, and so forth) or other similar systems.

The third party system(s) 140 can be in direct contact with or in close proximity to a particular user in order to obtain relevant sensory data. The third party system(s) can also include medical clearing houses, insurance entities, medical facilities, hospitals, medical labs, universities or other entities that store medical records and other medical information and which may be remotely located from the user or that are capable of obtaining sensory data or other environmental or anatomical condition data remotely from the user.

Figure 9:
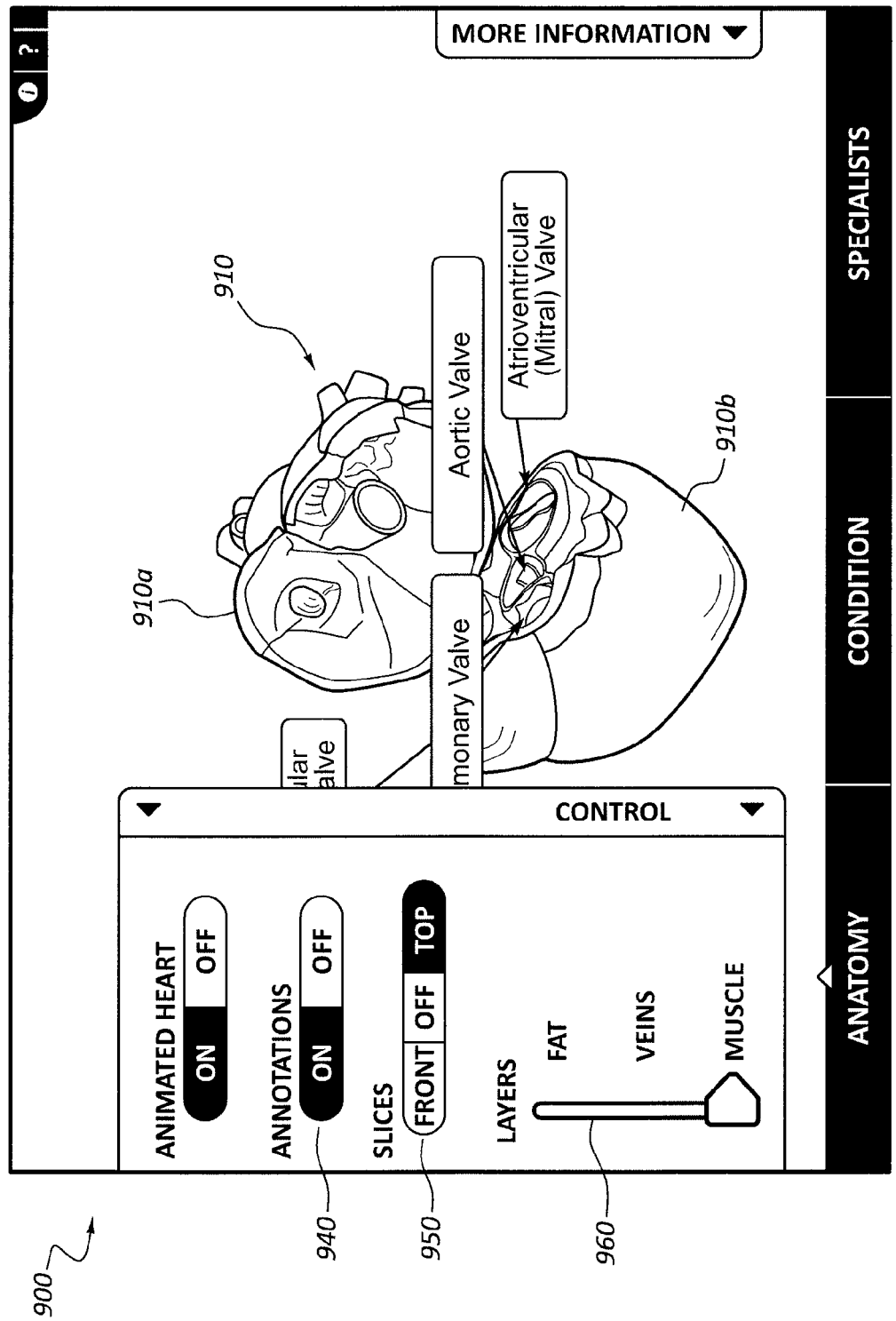
Figure 10:
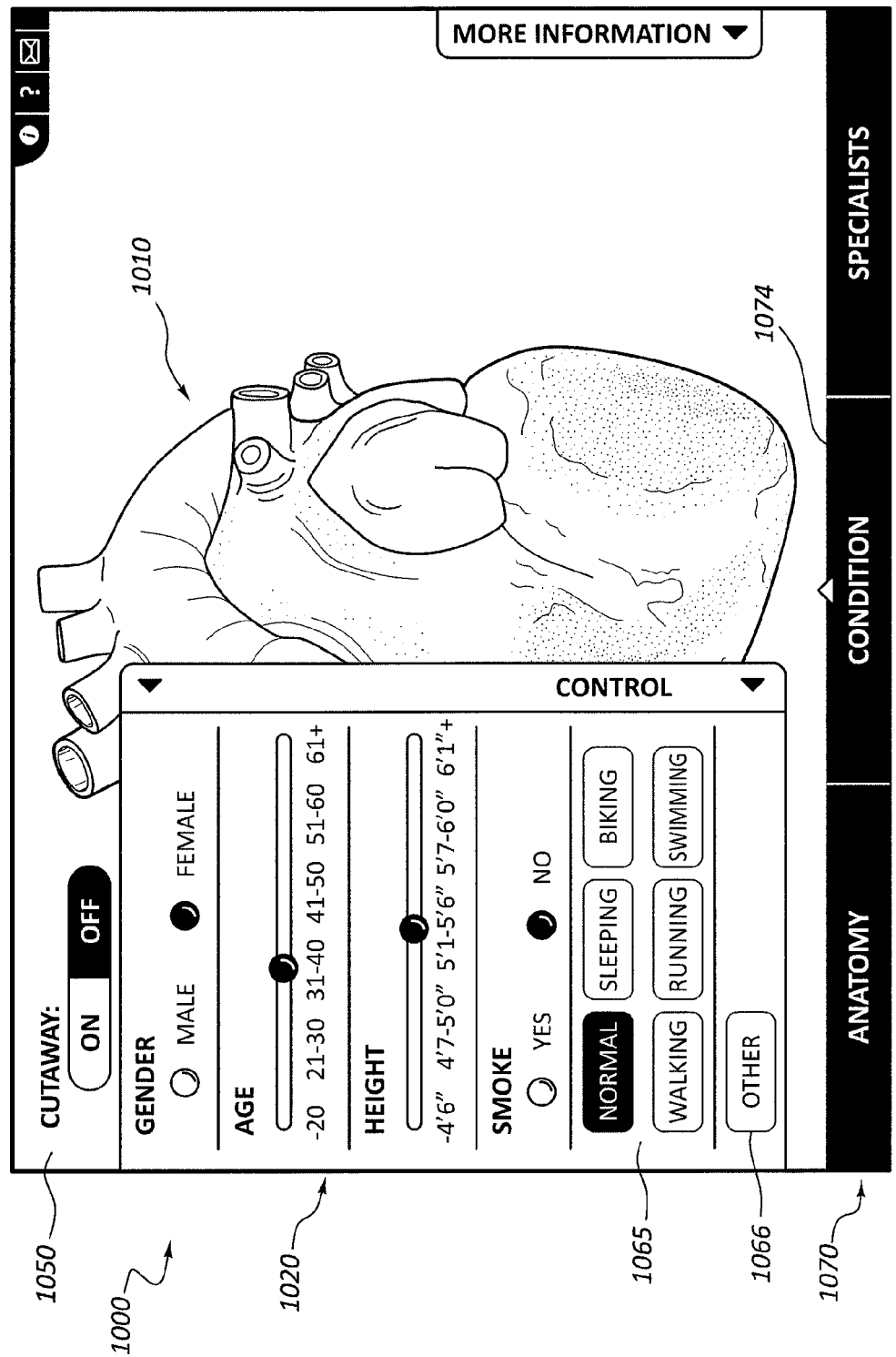
Figure 11:
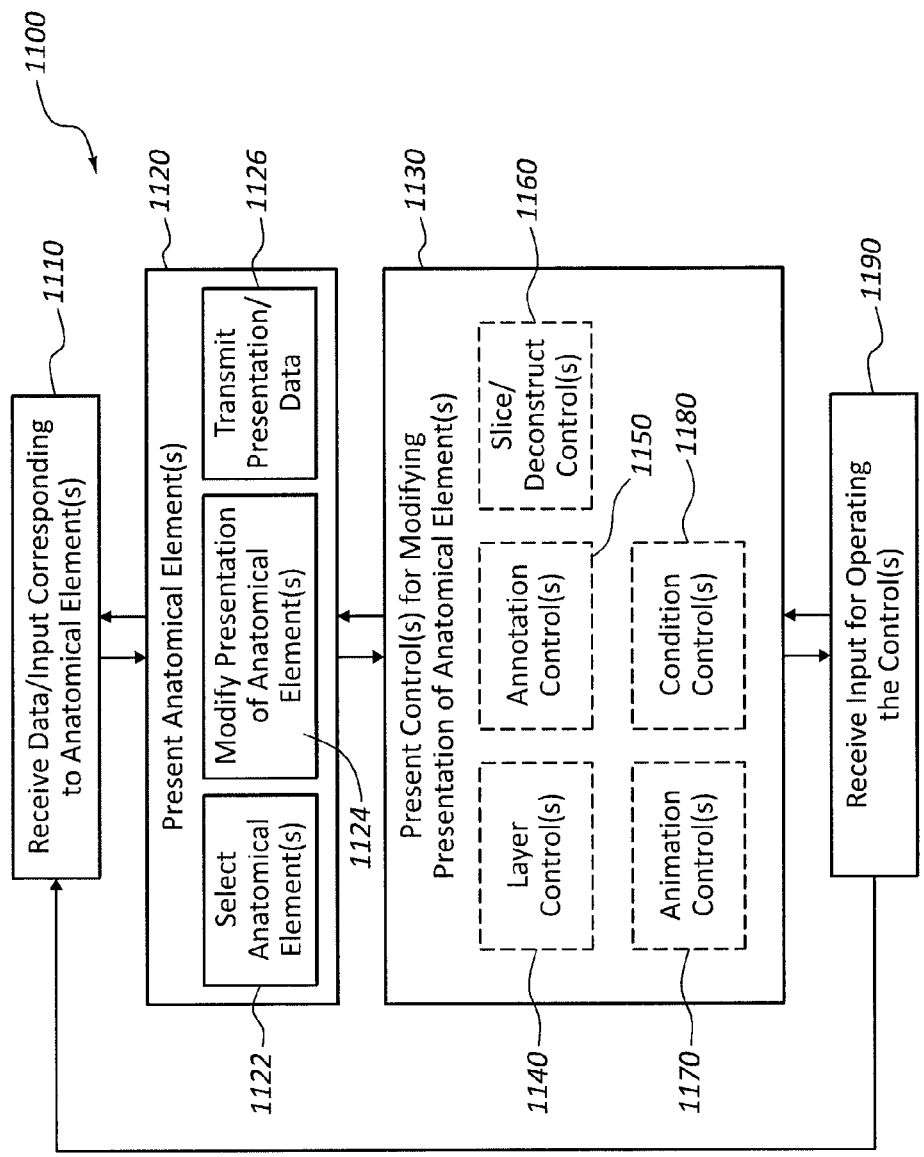
FIG. 11 illustrates a flowchart of acts associated with methods of the invention.

The following disclosure primarily relates to FIGS. 2-11. FIGS. 2-10 show various interfaces having features and controls that can be used to render anatomical elements and which, according to some embodiments, can be modified to correspond with personalized or relevant conditions for a particular user or anatomical element. FIG. 11, on the other hand, illustrates a flow diagram 1100 of various acts associated with some of the disclosed methods of the invention, including the identification and presentation of anatomical elements, and for demonstrably reflecting the impact of various conditions and treatments on the different anatomical elements.

FIG. 2

As shown, interface 200 includes a display window 202 for displaying one or more anatomical elements. Presently, the display window 202 is rendering a heart 210. In some embodiments, the heart 210 or other displayed anatomical elements are generic inasmuch as they are not personalized to any particular user. In other embodiments, however, the displayed anatomical elements are personalized insofar as the rendering of the anatomical elements is based at least in part on one or more variable conditions that correspond to a particular user. These variable conditions can include a state of physical fitness, a medical history, current environmental or medical conditions, detected sensory data, anticipated medical treatments, past/present/future lifestyles, medical diagnosis, computer modeling, and other such variables.

Currently, the displayed anatomical object (e.g., heart 210) is limited to only a single organ. It will be appreciated, however, that any quantity of one or more anatomical object(s) can be displayed at any given time, including any combination of one or more generic and/or personalized anatomical elements. For instance, although not presently shown, the display window 202 can display a first heart personalized for a first user, while also displaying a second heart that is somewhat generic (e.g., ideal or common) relative to the personalized heart. Alternatively, the second or a third displayed heart can be another personalized heart or organ corresponding to a family member or associate of the first user.

In another embodiment, the heart 210 can be displayed with an entire cardiovascular system and/or one or more additional organs (e.g., the brain, the liver, the lungs, etc.) that are either generalized or personalized for the user.

Selection of the anatomical element(s) to be rendered can be made automatically and/or manually. In some instances, for example, the rendering system receives instructions from a remote server or third party system to render one or more anatomical elements. Specific rendering instructions and graphics data can be stored at the client/rendering system or at the remote system(s) in communication with the client system.

The rendering instructions can include static data, which remains relatively unchanged over time (e.g., less than once an hour, day, week or less frequently), as well as dynamic data that changes relatively frequently (e.g., at least once a week, day, hour, minute, second, or more frequently).

Manual instructions can also be provided to select the anatomical element(s) that are to be rendered through one or more menu interfaces of the invention and which are accessible through selectable lists or other menus, such as by navigating through menu 270 to access corresponding submenus (not presently shown).

In some embodiments, the rendering system is linked to one or more sensors (e.g., heart rate monitor or other sensor) that provides sensory input to the rendering system through a wired or wireless connection and which causes the rendering system to automatically render anatomical element(s) associated with the sensory input in response to detecting/receiving the sensory input. The rendering of the anatomical element(s) can also be conditioned upon the satisfaction of one or more user definable criteria. For instance, by way of example, the rendering system can be configured to render a heart that is beating in response to detecting that the user's heart rate has exceeded or dropped below a particular heart rate based on data detected from a heart rate monitoring system that is gathering data about the user.

While the term 'render' is sometimes used interchangeably with the term 'display', and vise-versa, it will be appreciated that the term 'render' and 'display,' as used herein, have a broader connotation than to merely provide visual feedback. Instead, the terms 'render' and 'display' also apply to any type of presentation or simulation, including any combination of visual, aural and haptic feedback/output. Audio feedback, for instance, can be provided through speakers and haptic feedback can be provided through oscillating or vibrating hardware, which can be integrated into or otherwise operably connected to the systems of the invention.

The presentation of heart 210 via display window 202, for instance, can also include the rendering of audio feedback that simulates a beating heart or a verbal presentation of information about the heart, and/or haptic feedback that vibrates the display or another part of the rendering system to simulate the beat of the heart 210.

In some preferred embodiments, the haptic and/or audio feedback is synchronized with the visual feedback presented on display window 202. While the foregoing example clarifies how visual, aural and/or haptic feedback can correspond to the presentation of the displayed heart 202, it will be appreciated that the presentation of any combination of visual, aural and/or haptic feedback can be used to represent any combination of different anatomical elements.

In some embodiments, one combination of feedback (one or more of visual, aural and/or haptic feedback type(s)) is used to represent a first anatomical element (e.g., a heart or other element), while a different combination of feedback type(s) is used to represent a different anatomical element (e.g., the lungs). For instance, in one non-limiting example, haptic and aural feedback are used to present the simulation of a beating heart through sound and touch while a lung is visually presented with or without a visual presentation of the corresponding heart.

Figure 2:
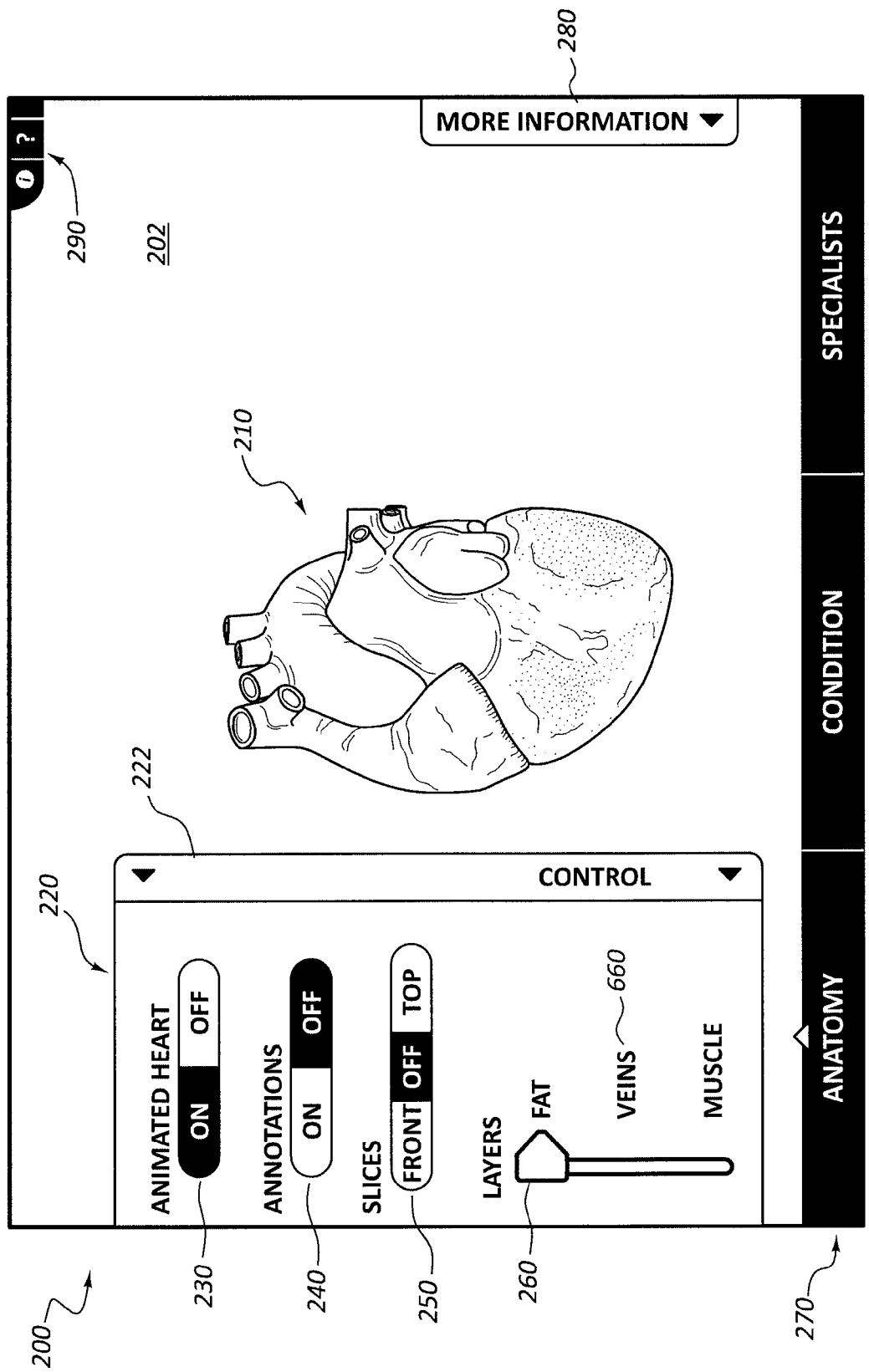
FIGS. 2-10 illustrate a few non-limiting examples of user interfaces that are capable of rendering anatomical elements, as well as controls and other interface components that are capable of being used to modify the rendering of the anatomical elements, according to some aspects of the invention.

FIG. 2 also illustrates a control bar 220 with a plurality of controls 230, 240, 250 and 260, which will be described below and which can be selectively used to manipulate or otherwise control the manner in which the anatomical element(s) will be rendered by initiating the execution of interface function calls associated with the controls when selected or otherwise manipulated by a user to perform the described functionality.

The controls can be exposed and accessed by selecting the control tab object, which is selectable to expand or maximize the control bar 220 when the bar is minimized or hidden (e.g., control tab object 322, FIG. 3) or to, alternatively, minimize or hide the control bar when the bar is expanded or maximized (e.g., control tab object 222, FIG. 2).

Animation control object 230 provides animation options for turning animations on or off. In some embodiments, animations present a video simulation, audio simulation and/or haptic sensation corresponding to the displayed anatomical element(s). In the present example, the animation control object 230 is turned on, such that the heart is rendered in a multimedia presentation as an actual beating heart. This beating heart can be synchronized with the beating of the user's heart by detecting input from a heart rate sensor and using the detected input to drive real-time modifications to the animation.

The animation control 230 can also be used in some embodiments to reflect degradation, improvement or other anticipated aging progressions of the rendered anatomical element(s) over time based on one or more conditional inputs. This animation can be viewed as a smooth simulation or discrete time lapse imagery with any combination of audio/haptic feedback. The conditional inputs that can be used to modify/control the animation can include any combination of a detected state of physical fitness, age, medical history, current environmental or medical conditions, detected sensory data, medical treatments, past/present/future lifestyles, medical diagnosis and computer modeling. In this manner, a user can view a personalized representation of anatomical element(s) and conditions associated with the user. Some of the techniques that can be used to provide this conditional data through interfaces of the invention are shown and described in more detail, below, with specific reference to at least FIG. 10.

Annotation control object 240 is used to control when annotations will be presented with the displayed anatomical elements. Annotations are described in more detail in reference to FIGS. 3-5 and 7-9. While the annotation control object 240 presently shows only on or off options, some embodiments include additional options, such as options for selecting the types of annotations that will be rendered, as well as the format for rendering the annotations (e.g., font attributes, color coding and labeling options for the anatomical elements, language type, aural and/or visual rendering options, and so forth).

Slice/deconstruct control object 250 is operable to define a format for displaying the anatomical elements. When turned off, as in FIG. 2, the anatomical element is rendered intact. When a 'front' option is selected, the anatomical element is rendered as though it were sliced along a vertical plane and laid open, as in FIG. 5. When a 'top' option is selected, the anatomical element is rendered as though it were sliced along a horizontal plane and laid open, as in FIGS. 4 and 9.

Different deconstruction options, besides top, front and off, can also be presented (although not presently shown) to operably control the manner in which the anatomical elements are visually rendered in different views (e.g., exploded, pealed, stretched, rotated, perspective, color-coded, and other views).

Layer control object 260 is operable, when used, to select the granularity at which the anatomical element(s) are displayed. In the present example, the layer control object 250 is used to select a fat layer, a vein layer or a muscle layer. In other embodiments, the layers are replaced with levels of depth, systems, assemblies and subassemblies, types, granularities, conditions, anatomical elements, granularities or any other options associated with a hierarchical or ordered display scheme.

As shown in FIG. 2, the layer control object 260 is set at the fat layer. According to one embodiment, the fat layer is the layer of an organ (e.g., the heart 210) below the veins and enveloping ancillary muscles. In other embodiments, the fat layer is selected to render the presence and location of fatty tissues.

Figure 6:
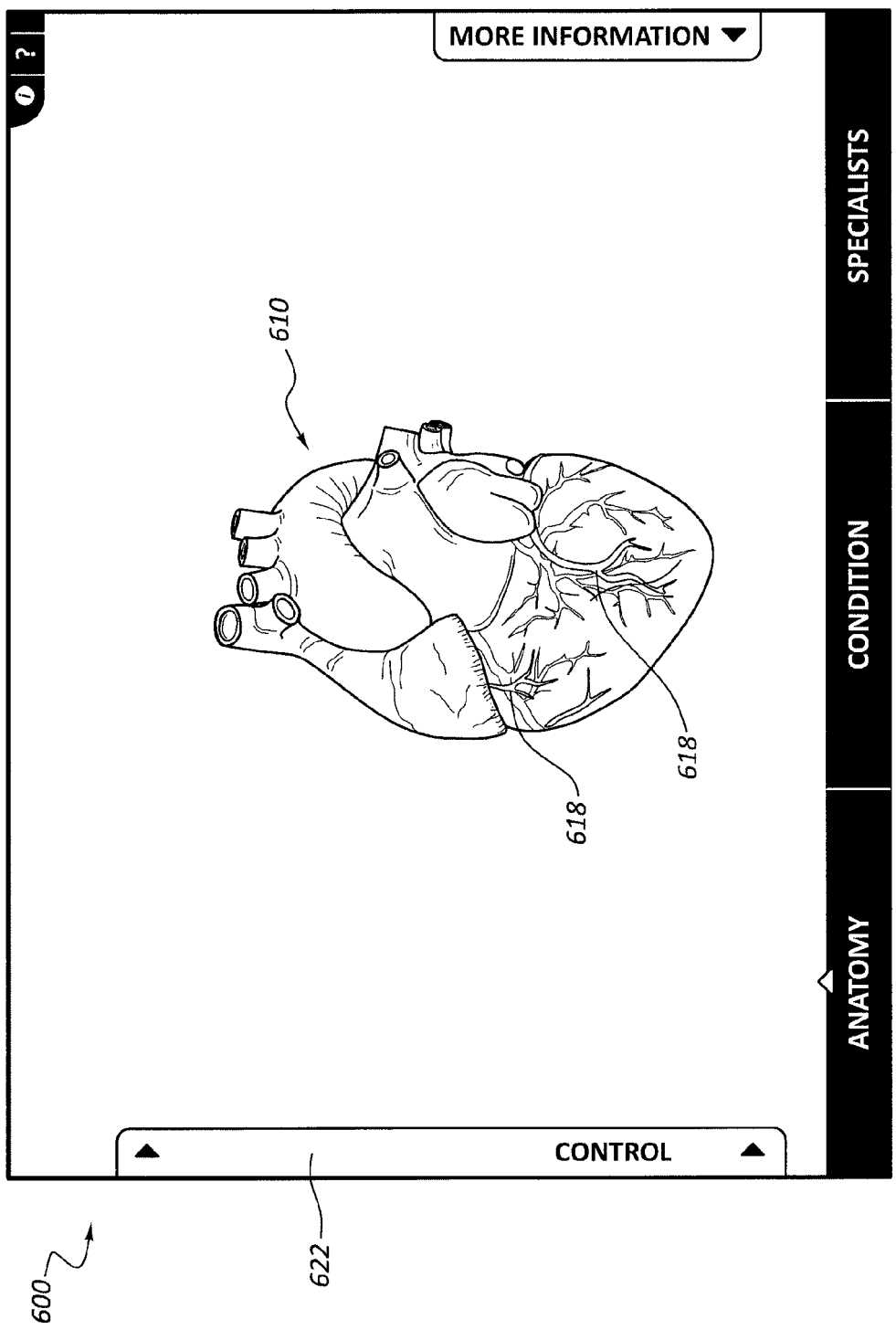
Figure 7:
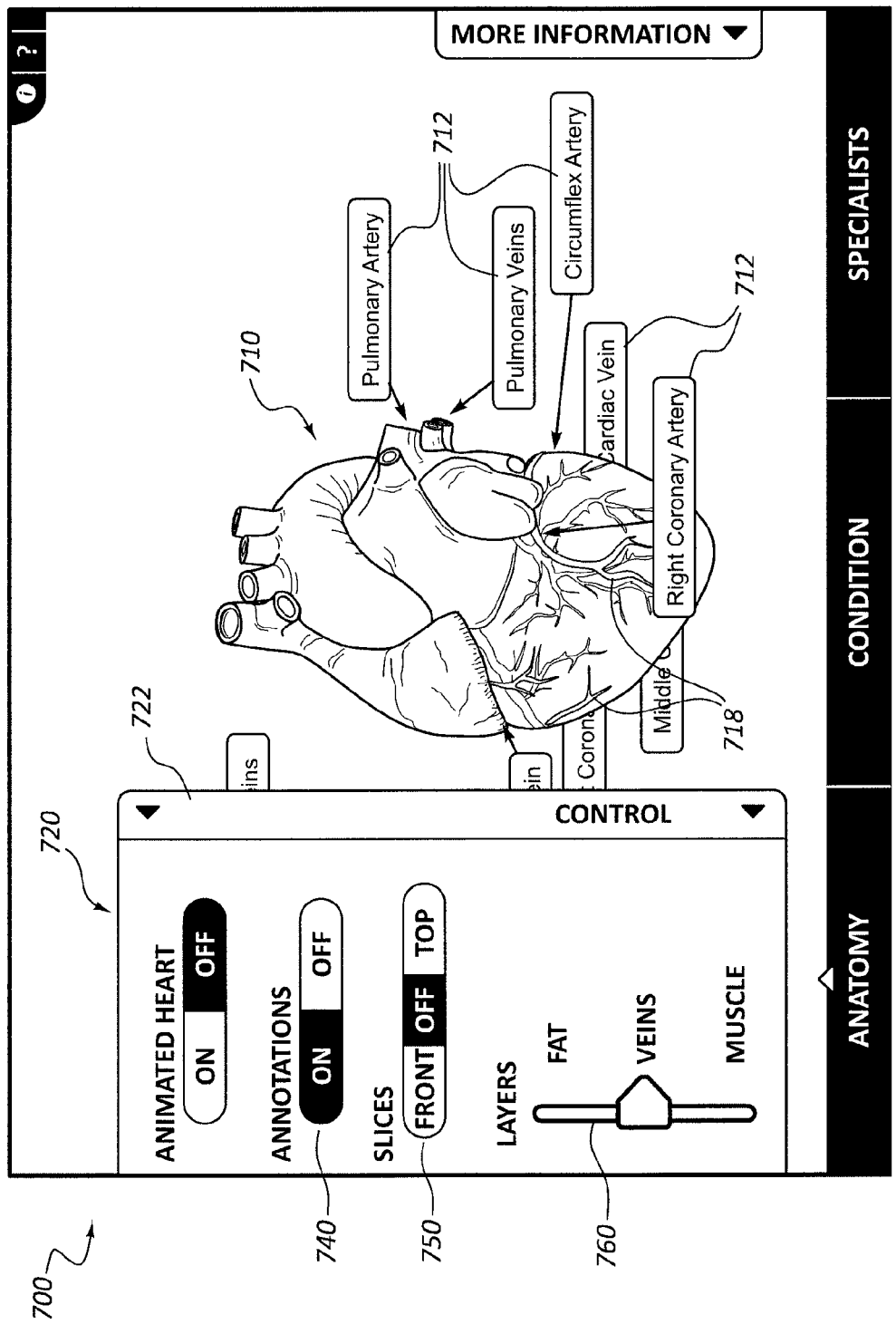

When the vein layer 660 is selected, anatomical element(s) are displayed with veins, as shown in FIGS. 6 and 7. Alternatively, only veins are shown for a defined structure.

Figure 8:
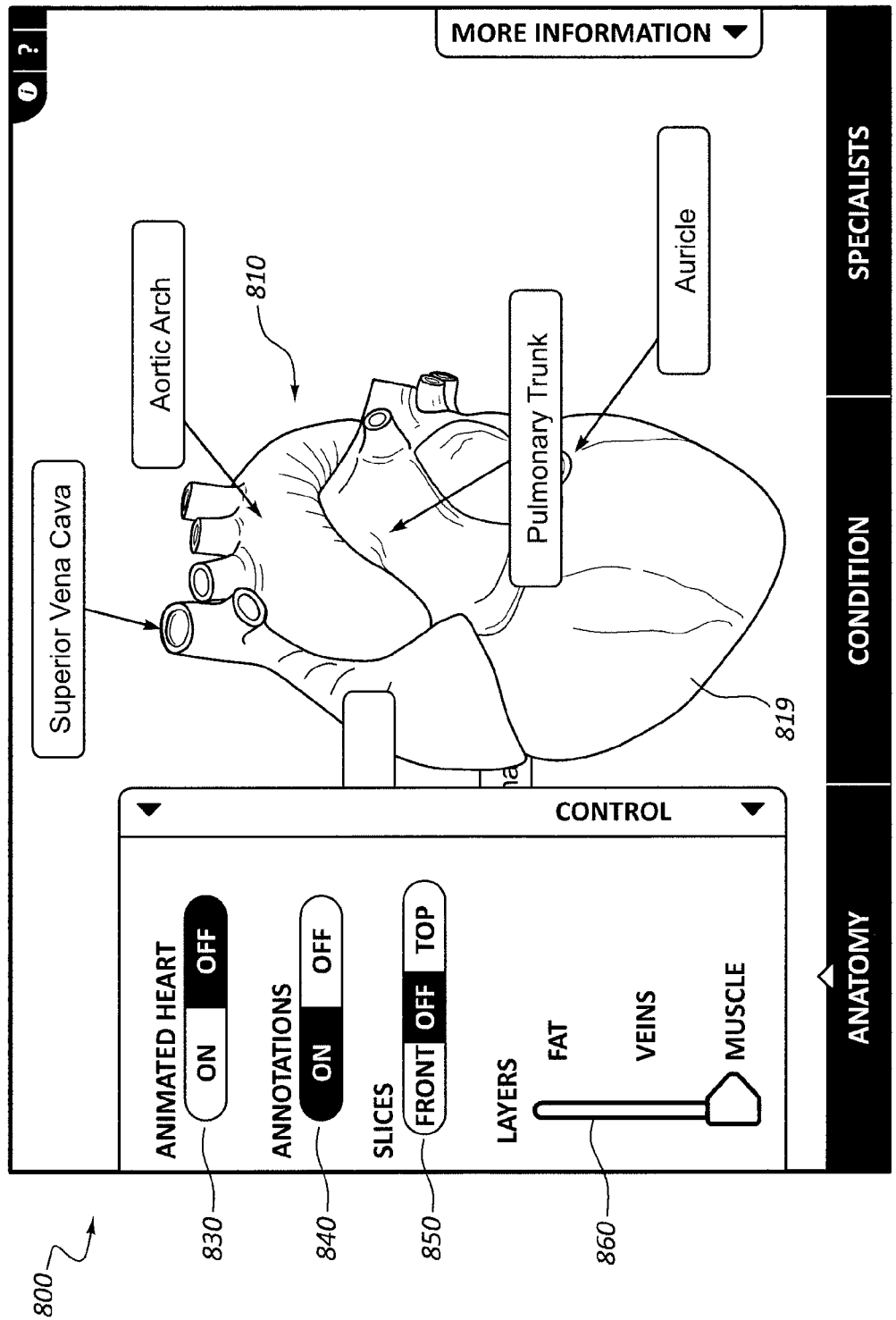

When the muscle layer is selected, as shown in FIGS. 8-9, the anatomical elements(s) are displayed with muscle tissues that drive, support, envelope, underlay or otherwise correspond to the anatomical element(s). Different predefined and/or selectable criteria can be used to determine which related muscle tissues will be rendered with the anatomical element(s). In some embodiments, the layer control object 260 includes additional displayed options for selecting the criteria or muscle tissues to be rendered.

Although not presently shown, the control bar 220 can also include other control options for modifying specific audio/haptic/visual properties used to render the anatomical element(s), including but not limited to volume controls, brightness and color controls, speed and intensity controls. Additional controls, not presently shown, can be displayed on the control bar 220 for selecting different anatomical element(s) to display and the sources of conditions or other information that will be used to control the rendering of the anatomical elements. Some controls, not presently shown, can also be used to select or control criteria for receiving or transmitting information related to the anatomical elements(s) between any number of different server, client and third party systems and how the information is transmitted (e.g., communication channels, formatting, security, validation, and so forth) and when that information is transmitted (e.g., time of transmission, frequency, transmission triggers, and so forth).

FIG. 2 also illustrates a navigation menu 270 that can be used to access some of the interface controls and elements described herein. For instance, when the 'anatomy' option is selected, the interface 200 presents control bar 220. However, when the 'condition' option is selected, a different control bar can be presented, as shown in FIG. 10.

Selection of the 'specialists' option results in the presentation of an interface display that reflects information for finding or contacting a specialist, such as, but not limited to, specialists associated with the rendered anatomical element(s). This display can also present a map and/or routing information for finding or traveling to a location associated with the specialists. Sometimes, pricing information can also be provided, to reflect estimated fees associated with treatments or care for conditions associated with the rendered anatomical element(s). The pricing information and other specialist information can be filtered according to any predetermined criteria, including user insurance coverage, user location, time of day, traffic conditions, determined urgency, or any other variable.

Filtering of information can be useful when a condition associated with a user requires immediate attention, so as to expedite the manner in which the user can contact and/or reach the specialist for necessary information and/or treatment. Access to and the filtering of information can be provided automatically using of the client, server or third party systems described herein, responsive to predefined criteria and detected conditions. Access to the information and filtering can also be performed manually at any of the disclosed systems in response to manual input entered at the systems.

While filtering has been specifically described with regard to the 'specialists' option from menu 270, it will be appreciated that corresponding and similar filtering can be used to selectively access and render any information described herein and which can be accessed through any of the interface components of the invention.

In some embodiments, additional information can be provided through additional menu objects, such as the more information object 280 or information controls 290.

All of these objects, as well as the other interface elements described herein (e.g., the controls, annotations, displayed layers and other anatomical elements) are configured, according to some embodiments, as interactive links which, when selected, initiate a software function call to access and render additional information corresponding to the selected element and/or to initiate one of the functions described herein and that are associated with the claimed invention.

FIG. 3

Figure 3:
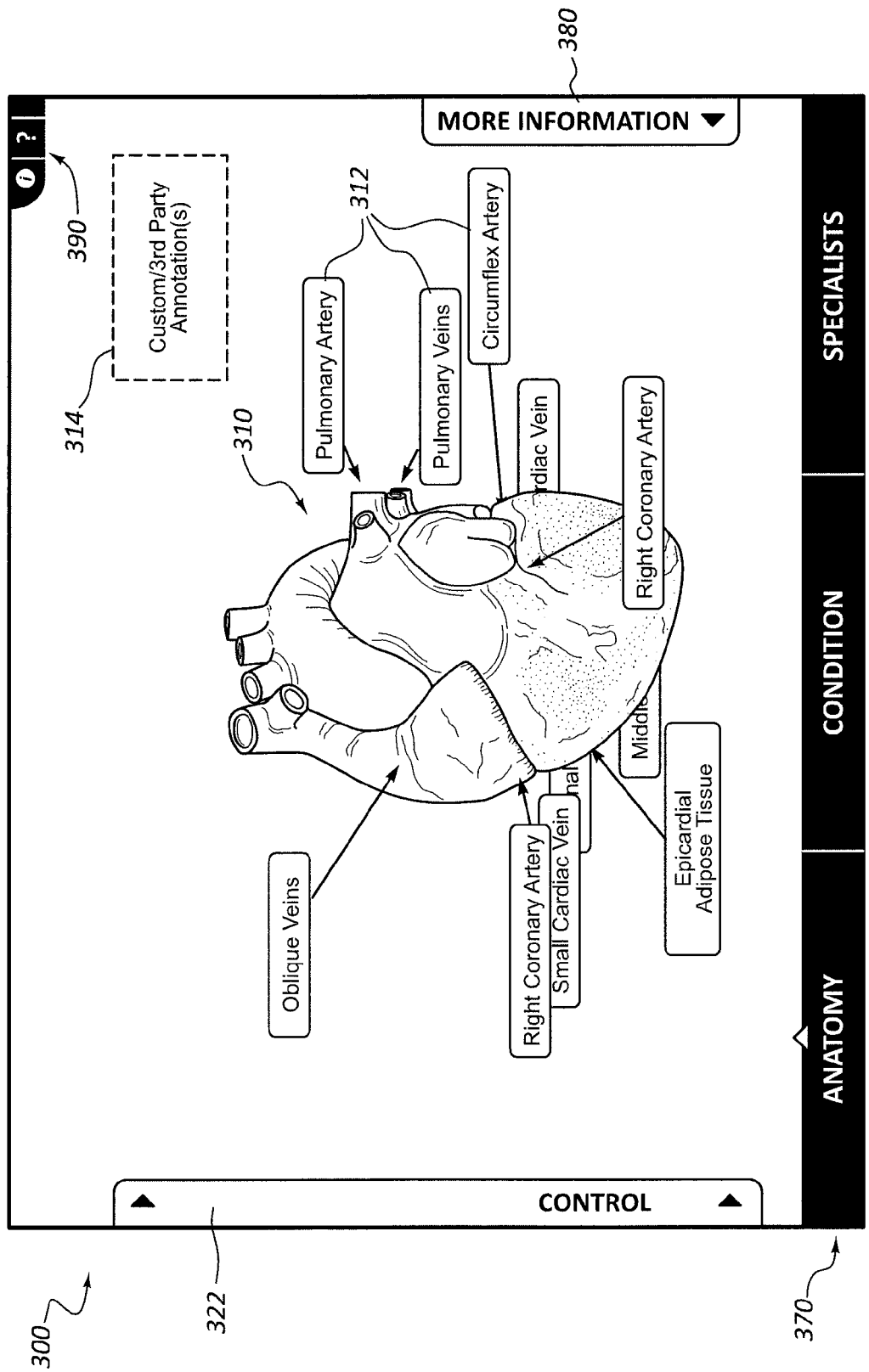

FIG. 3 illustrates another interface 300, which is similar to the interface 200 of FIG. 2, and which is rendering a heart 310. In this embodiment, controls for determining how the heart 310 will be presented are currently hidden. However, they can be exposed by selecting control tab object 322. These controls, when exposed, can include an annotations control (similar to annotations control 240) to define whether annotations will be rendered with the anatomical elements.

The annotations control can also be used, in some embodiments, to select what types of annotations will be presented and the manner in which they will be presented. These annotations can include a user's personal annotations, a medical professional's annotations, third party annotations and/or any other annotations that are accessible to the rendering system. These annotations can be generated at any combination of the client, server and third party systems.

As presently shown, various annotations (including annotations 312) are used as labels to identify different components of the illustrated anatomical element(s). These types of annotations can be provided by a medical clearinghouse, for example, or an educational institution, and/or the software manufacturer. Different types of annotations from different sources can be presented at a same time in some embodiments, or separately, depending on selected control settings (such as can be selectively set through the 'condition' option of menu 370, the information controls 380, 390, and/or menu options that are displayed in response to a selection of control 322).

As further shown, some annotations are provided as custom or third party annotations 314 that are linked to the rendered anatomical element(s) by the user, a medical professional, an insurance carrier, and/or another entity or system. These annotations 314 can include treatment options, medical records, notifications, warnings, instructions, descriptions or other information related to the rendered anatomical element(s). These other annotations 314 can be presented simultaneously with the anatomical element(s) and/or separately.

According to some embodiments, as indicated above, the annotations 312 and/or 314 are interactive links, as are the graphical objects/elements to which they point or correspond. For instance, each annotation/label 312 is operable to render additional information when selected. Similarly, discrete portions of the displayed heart 310 are individually or collectively operable, when selected, to render additional information corresponding to the rendered anatomical element(s) or to initiate a functionality (e.g., prompting the user for annotation data, triggering a new modified display of the anatomical element(s) via the slice/deconstruct control, layer control or animation control, and so forth).

FIG. 4

Figure 4:
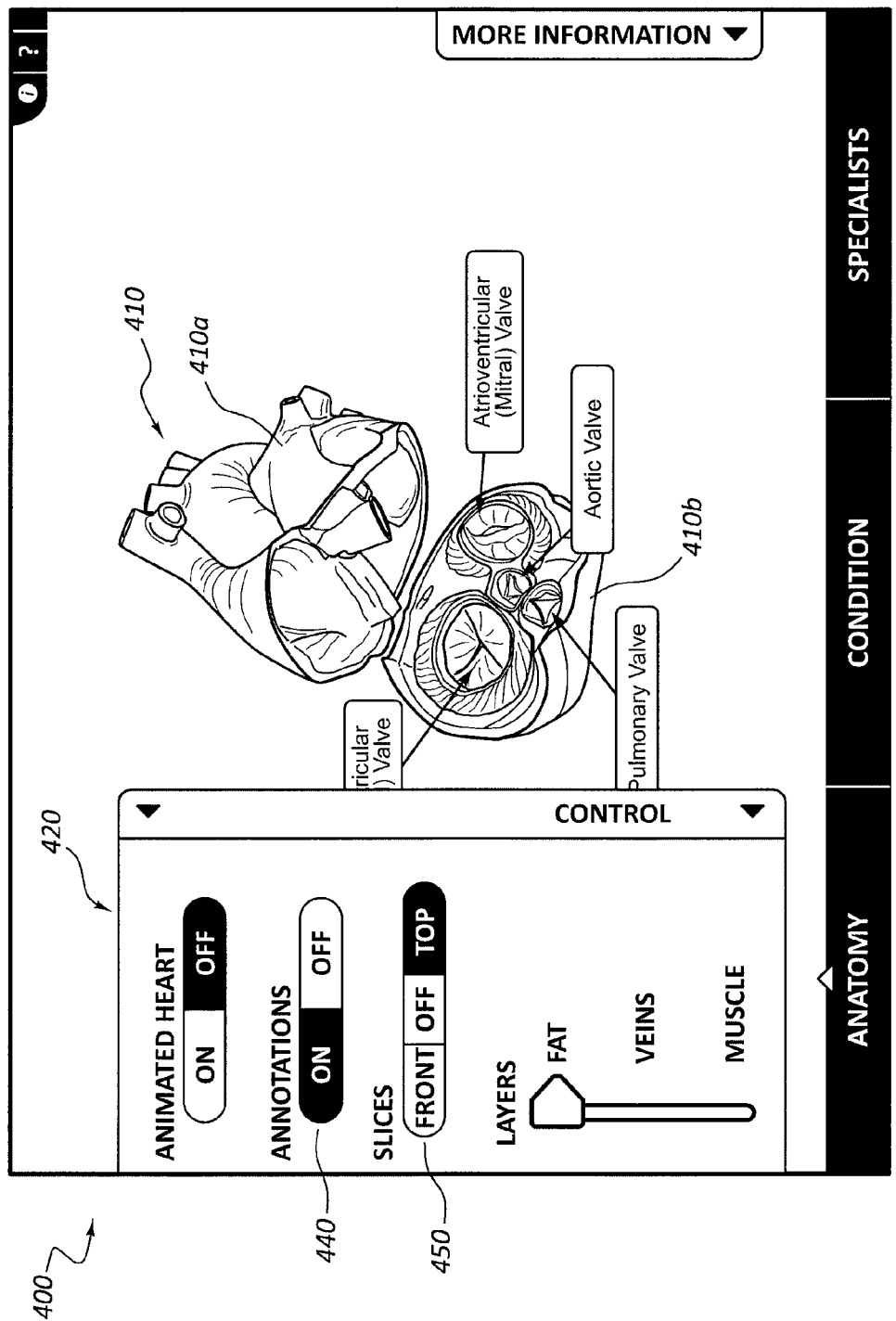

FIG. 4 illustrates another interface 400 with a rendered heart 410 which is split into two halves 410a and 410b along a horizontal plane, corresponding to the slice/deconstruct control object 450 being set to the 'top' view option. As shown, the annotations control object 440 is also set to on, such that corresponding annotations are presented as labels that point to discrete portions of the rendered heart 410.

While the animation control object is set to off, it will be appreciated that the inner workings of the heart could be visible and simulated in motion by setting the animation control object to on.

FIG. 5

Figure 5:
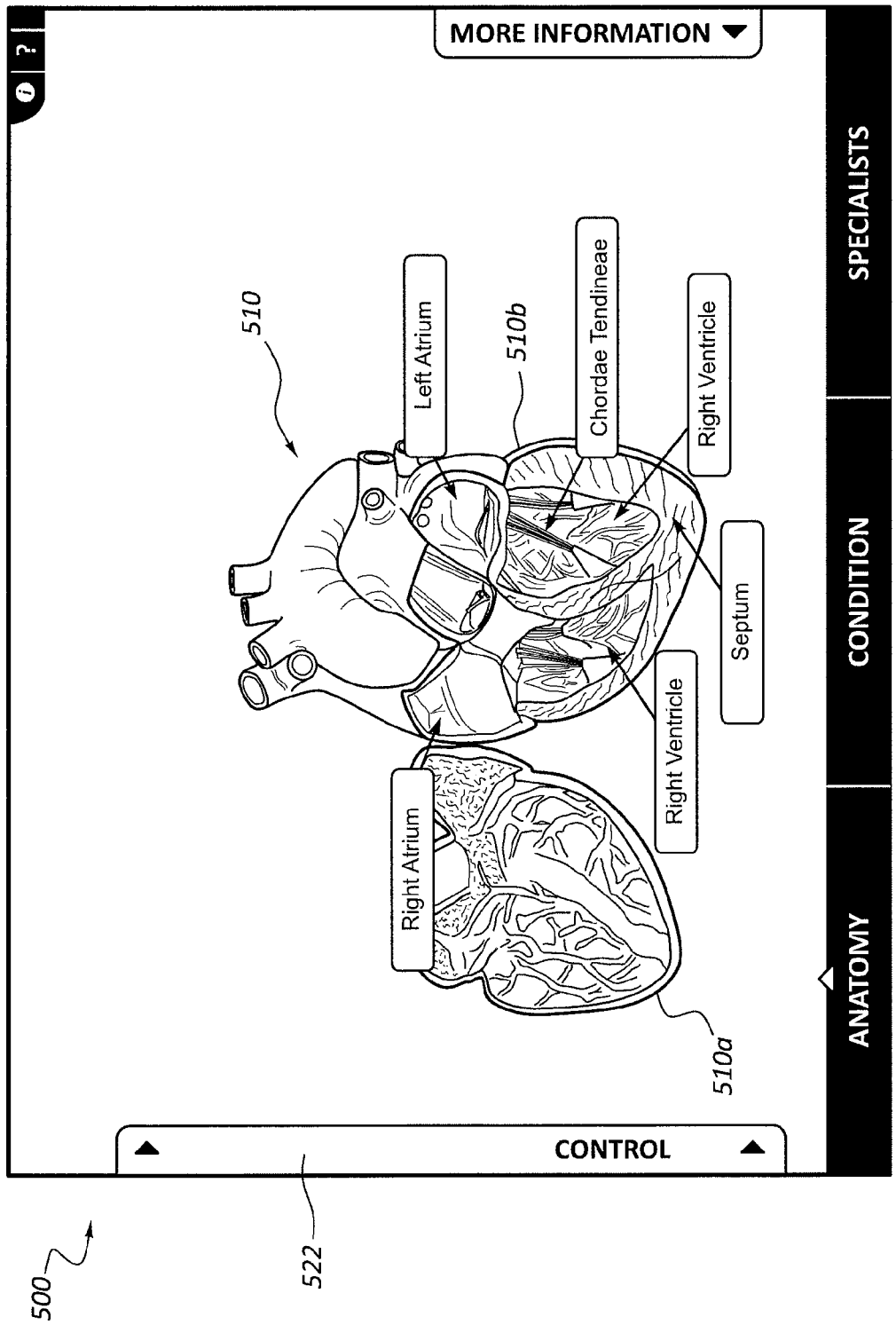

FIG. 5 illustrates interface 500 having a rendered heart 510 which is split into two halves 510a and 510b along a vertical plane, corresponding to the slice/deconstruct control object being set to the 'front' view option (not shown since the control tab object 522 is hiding the controls).

While heart 510 is shown as being split into exactly two slices, it will be appreciated that the slice/deconstruct control objects of the invention can be used to select any number of preferred slices to display, including 3 or more, for any particular/selected portion of the displayed anatomy.

FIG. 5 also includes annotations, thereby indicating that an annotations control (such as annotations control 240) has been set to on.

FIG. 6

FIG. 6 illustrates interface 600 having a rendered heart 610 which is displayed with veins 618, thereby indicating that a vein layer has been selected on a layer control object (such as layer control object 260) which is accessible by selecting control tab object 622 or another menu interface object. Other hidden controls include an annotations control object set to off and a layer control object is set to fat.

FIG. 7

FIG. 7 illustrates interface 700 having an exposed control bar 720 which can be hidden in response to a selection of the control tab object 722. The control bar 720 includes an annotations control object set to on a slice/deconstruct control object set to off and a layer control object 760 set to veins. Accordingly, heart 710 is responsively displayed with labels 712 and veins 718.

FIG. 8

FIG. 8 shows an interface 800 that is rendering a heart 810 with labels and heart tissue 819 in response to the annotations control 840 being set to on, the slice/deconstruct control object 850 and animation control object 830 being set to off, and the layer control object 860 being set to muscle.

FIG. 9

FIG. 9 shows an interface 900 with a heart 910 rendered according to selected controls, in which the heart 910 is split into two halves 910a and 910b along a horizontal plane, corresponding to the slice/deconstruct control object 950 being set to the 'top' view. The annotations control 940 is also set to on, and the layer control object 960 is set to muscle, thereby causing the heart 910 to be rendered accordingly.

FIG. 10

FIG. 10 illustrates yet another example of an interface 1000 of the invention. In this embodiment, a heart 1010 is rendered according to controls/settings that were described above in reference to FIGS. 2-9, and which can be accessible through the 'anatomy' option, or another interface menu option.

FIG. 10 illustrates a different set of controls 1020 that can be accessible through the condition 1074 tab of menu 1070 and which can be used to select one or more conditions that impact the manner in which the rendered anatomical element(s) will be displayed. This set of controls 1020, for example, can be used to personalize the rendered anatomical element(s). In particular, the controls 1020 can be used to identify an age, height, gender and other information (e.g., activity level 1065 and other information 1066) that can affect the development of the user's anatomy. This information is then used by computer models and statistical data to modify how the anatomical elements (e.g., heart 1010) associated with the user will be displayed.

Other types of input controls can also be provided through control 1020, (although not presently shown), to identify a user's state of physical fitness, medical history, current environmental or medical conditions, detected sensory data, anticipated medical treatments, past/present/future lifestyles, medical diagnosis, equipment being used by the user, sources for information, and other information. Any combination of this information can be used to modify how the rendered anatomical element(s) will be presented by using this information in combination with statistical records and computing models associated with the anatomical element(s).

As new information is received, the rendering of the anatomical element(s) can be dynamically modified, even in real-time, such as, for example, when a user is undergoing a treatment, taking a drug, exercising, and so forth.

While a user can explicitly and manually provide the information, as described above, it will be appreciated that any of this information corresponding to the user can also be obtained automatically by the rendering or related server/third party systems having access to the user's medical records and system data to help personalize the manner in which the rendered elements are presented and/or modified.

Some non-limiting examples of how the controls of the inventive interfaces can be used to obtain data that is, in turn, used to control the presentation of the rendered anatomical elements will now be provided.

In one example, a patient is educated about lifestyle choices and consequences of bad choices by providing conditional data, via the controls described above and/or by providing access to medical records and sensory data that is capable of being used with statistical data and modeling algorithms by the interfaces of the invention to simulate the patient's existing anatomy and to present simulations of degradation of various anatomical elements that are personalized to the patient's data.

Similarly, the patient can view different simulations that correspond to different combinations of input data, including anticipated changes in behavior (e.g., stop smoking, start exercising, and so forth) to view how the changes will affect one or more of the rendered anatomical element(s). The simulations can also be compared side by side or sequentially to provide even more of an impact on the patient.

Similar simulations can be run to reflect the anticipated impact of various treatments on the anatomical element(s) or to show the impacts on one anatomical element can trigger corresponding changes in other rendered anatomical elements for similar or different anatomical systems.

In another example, a runner that has a heart monitor is able to view a simulation of their heart beating while they exercise. The heart monitor provides input that is received and used to drive modifications to the rendered heart on the interfaces of the invention. Accordingly, the simulated heart on the runner's phone, tablet or other electronic device is programmed with the interfaces of the invention to render simulations that mimic the real time heartbeat of the runner and to provide other relevant cardiovascular information. This information can be used to help provide instructions for optimal training and to avoid exceeding unsafe thresholds.

With proper sensors to monitor air flow, it is also possible to identify the breathing behaviors of a user and to provide desired information regarding lung capacities and the volume of oxygen consumed during exercise. This type of information can be presented with simulations of the lungs or entire pulmonary system that are personalized to a particular user based on any number of conditional input data described above, including exercise data.

In other examples, the interfaces of the invention simulate or warn a user regarding catastrophic conditions, such as heart attacks, seizures, strokes, diseases, and other conditions, to thereby help educate the users regarding possible risks and effects of these conditions.

When existing conditions that are being monitored in real-time present information to the interfaces that are determined to meet or exceed certain conditions, it is also possible to generate a warning that is rendered on the interfaces and/or that is transmitted to one or more other systems and devices, such as the devices of a loved one or a caregiver. In some instances, the warnings can be used to perform triage services and to even initiate emergency services, such as an ambulance service. For instance, upon detecting conditions that indicate a user is experiencing a heart attack, a seizure, a stroke, an insulin or other chemical deficiency or overload, and/or any other predefined condition, it is possible to access instructions and contact information for imitating the generation of a message or a call to one or more systems, as described above. The generation of the message can also include personalized information for the user to route the user to a best option for medical treatment (e.g., closest, covered by insurance, specialist, and so forth).

In another embodiment, a user is connected to neurological sensors that identify responses and that are used as input to simulate neurological activities in response to one or activities and conditions.

Simulations, such as the foregoing, can also be presented with the interfaces of the invention by using hypothetical or estimated input/conditions that are determined to correspond to a particular user and so as to personalize the simulations, even without using real-time sensory data.

In other embodiments, a simulation can be performed by the interfaces for a complex system, such as an entire human body, such as, for example, to dynamically simulate a particular user's body as it undergoes changes in weight based on known and anticipated conditional data that is provided to the interfaces. The simulated body can be personalized to the specifications of the user's body before the simulation begins.

It will be appreciated that any existing modeling techniques and algorithms can be used to provide smooth and accurate transitions for any renderings presented according to the claimed invention. In particular, the interfaces of the invention utilize modeling instructions which correlate variable inputs to potential or known output model feedback. The variable inputs can be used, therefore, to drive the rendering of the simulations, animations and other outputs described herein. In some embodiments, the inputs are data accessed by the client, server and/or third party systems and the outputs are audio, video and/or haptic feedback controlled at least in part by the inputs.

FIG. 11

Attention will now be directed to the flow diagram 1100 of FIG. 11, which includes various acts associated with some of the disclosed methods of the invention and which are generally described above in reference to FIGS. 1-10.

The illustrated acts include, for example, receiving data or other input corresponding to the anatomical elements that are to be rendered, or that are currently rendered and that are to be modified or for which supplemental information is to be made available (act 1110). This information can be entered through the controls of the inventive interfaces at the rendering/client system, or can be received from servers and third party systems, as described above. This information includes visual, audio and/or haptic feedback data that is capable of being used by rendering modules of the rendering system and corresponding hardware to render the visual, audio and/or haptic feedback in such a way as to provide images, sounds and/or touch output that simulates or otherwise represents anatomical element(s) and related information (e.g., pictures, video data, sounds and vibrations that illustrate, mimic or correspond to the anatomical element(s)).

The invention also includes presenting the anatomical objects/elements according to any of the techniques described throughout this disclosure, as well as the disclosure of the other applications referenced above (act 1120). In some embodiments, the presentation of the anatomical elements includes a manual selection of the anatomical element to be displayed (act 1122) through the inventive interfaces. In other embodiments, the presentation of the anatomical elements is made automatically, as described above, in response to detecting the satisfaction of predetermined criteria (e.g., receipt of input from the user or another entity, detected medical conditions, third party software instructions, transmission triggers, or other criteria).

The presentation of the anatomical element(s) (1120) can also include modifying (1124) a presently rendered anatomical element, or simply a modification of a record, annotation, setting, input or other information associated with the rendered anatomical element and which may or may not affect the video, audio and/or haptic feedback used to render the anatomical element.

The presentation of the anatomical element(s) 1120 can be made at the client system, the server and/or a third party system. In one embodiment, for example, it can be beneficial to transmit the presentation data (1126) to a medical professional or facility to aid in diagnosing and recording medical conditions relevant to the user for future benefit to the user and the medical community at large. This information can also be used, at times, to facilitate the emergency treatment of a user and to provide appropriate triage services (e.g., routing the user to an appropriate specialist, contacting the specialist, processing insurance claims, communicating with emergency contacts, transmitting medical information to appropriate specialists and other medical personnel, and so forth). All of these services can be automatically initiated and processed according to the scope of the invention, by using the information that is obtained by the inventive interfaces, such as, for example, by detecting certain conditions associated with the user that are determined to satisfy predetermined criteria for triggering any combination of the triage services.

To protect the privacy of the user, various control settings can be used in the interfaces to establish conditions for access to the medical information.

The presentation of the anatomical element(s) (1120), with or without modification (1124), is largely, but not always entirely, dependent upon input that is received (1190) via the controls that are presented to the user (1130), as described above. These controls can include layer controls 1140, annotation controls 1150, slice/deconstruct controls 1160, animation controls 1170, variable/personalizing condition controls 1180, as described above, or any other controls that would be understood by those of skill in the art to perform the claimed invention.

It will be appreciated that the foregoing acts of flow 1100 can be performed by any combination of the client, the server and/or third party systems described herein and can be performed in various ordering and are not, necessarily, mutually inclusive or exclusive.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A computer-implemented method for presenting anatomical information as one or more rendered anatomical elements and for modifying the rendering of the anatomical elements in response to conditional input data, the method being implemented on a computing system that includes a memory, at least one processor and a storage device having stored instructions which, when executed by the at least one processor, implement the method, the method comprising:

the computing system receiving input corresponding to an anatomical element and that is capable of being used by the computing system to represent the anatomical element;

the computing system presenting the anatomical element as at least visual object rendered on a display screen;

the computing system presenting controls for modifying the presentation of the anatomical element, the controls comprising:

at least a first control selected from the group of a layer control, an annotation control, an animation control or a deconstruct control presented through a first menu option on an interface, and at least a second control presented through a second menu option on the interface for personalizing the anatomical element to a particular user; and the computing system modifying the anatomical element in response to detected user input entered with at least the first or second control; and the computing system presenting a specialist link simultaneously with the first and second control and the presentation of the anatomical element which, when selected, displays contact information for one or more specialists associated with the anatomical element.

2. The method of claim 1, wherein the computing system is a distributed system.

3. The method of claim 1, wherein the anatomical element comprises an organ.

4. The method of claim 3, wherein the organ comprises a heart.

5. The method of claim 1, wherein the anatomical element comprises an anatomical system that includes a plurality of interconnected anatomical elements.

6. The method of claim 1, wherein the controls comprise both of the first and second controls.

7. The method of claim 1, wherein presenting the anatomical element further includes generating visual and audio output that each simulates at least one aspect of the anatomical element.

8. The method of claim 1, wherein the presenting the anatomical element further includes generating visual, audio and tactile output that each simulates at least one aspect of the anatomical element.

9. The method of claim 1, wherein first control includes each of the following controls as selectable interface objects:

the layer control which is operable, when selected, to control which of a plurality of different layers are to be displayed as part of the anatomical element, the annotation control which is operable, when selected, to control the presentation of annotations that are displayed with the anatomical element, the animation control which is operable, when selected, to control animations associated with the presentation of the anatomical element, and the deconstruct control which is operable, when selected, to select a deconstructed view of the anatomical element.

10. The method of claim 1, wherein the second control includes selectable options for defining a user's gender, age, height and activity level, and wherein input from each of these options is used to modify how the anatomical element is rendered.

11. The method of claim 1, wherein the second control includes selectable options for defining a medical condition of the user and which is used to modify how the anatomical element is rendered.

12. The method of claim 11, wherein the medical condition is a determination as to whether the user smokes.

13. The method of claim 11, wherein the method further includes receiving additional information from at least one remote server or third party system that is used to further modify the anatomical element.

14. The method of claim 13, wherein the additional information comprises a medical record.

15. The method of claim 1, wherein the method further includes:
   receiving real-time data from a sensory device that is sensing the real-time data for at least one anatomical element from a living being; and
   using the real-time data to modify how the anatomical element is rendered by the computing system so as to simulate the anatomical element with the computing system in such a manner as to mimic the anatomical element from the living being.

16. A computing system method for presenting anatomical information as one or more rendered anatomical elements and for modifying the rendering of the anatomical elements in response to conditional input data, the computing system comprising: a memory; at least one processor; and a storage device having stored instructions which, when executed by the at least one processor, implement a method comprising receiving input corresponding to an anatomical element and that is capable of being used by the computing system to represent the anatomical element; presenting the anatomical element with at least visual feedback; presenting controls for modifying the presentation of the anatomical element, the controls comprising:
   an animation control which, when selected, selectively turns on and off animations of the anatomical element,
   an annotations control which, when selected, selectively turns on an off a display of labels associated with different components of the anatomical element a slices control displaying at least three selectable options which, when any of the at least three selectable options is selected, causes the anatomical element to be displayed with a corresponding slice view
   a layers control displaying at least three selectable options which, when any of the at least three selectable options is selected, causes the anatomical element to be displayed with one or more corresponding layers associated with a selected option
   the animation control, the annotations control, the slices control, the layers control and the anatomical element all being displayed simultaneously; and at least a medical condition control which, when selected, is operable to receive input for personalizing the anatomical element to a detected medical condition associated with the particular user; and
   modifying the anatomical element in response to detected user input entered with at least the medical condition control.

17. The system of claim 16, wherein the system comprises a portable wireless device.

18. The system of claim 16, wherein the modifying of the anatomical element causes the anatomical element to be rendered by the system in such a way as to simulate a corresponding anatomical element of the user.

19. A recordable-type hardware storage device having stored computer-executable instructions which, when executed by one or more processors, implement a method for presenting anatomical information as one or more rendered anatomical elements and for modifying the rendering of the anatomical elements in response to conditional input data, wherein the method includes:
   receiving input corresponding to an anatomical element and that is capable of being used by the computing system to represent the anatomical element;
   presenting the anatomical element with a visual image on a display device;
   presenting controls for modifying the presentation of the anatomical element, the controls comprising:
      an animation control which, when selected, selectively turns on and off animation of the anatomical element;
      an annotations control which, when selected, selectively turns on and off a display of labels associated with different components of the anatomical element;
      a slices control displaying at least three selectable options which, when any of the at least three selectable options is selected, causes the anatomical element to be displayed with a corresponding slice view; and
      a layers control displaying at least three selectable options which, when any of the at least three selectable options is selected, causes the anatomical element to be displayed with one or more corresponding layers associated with a selected option;
      the animation control, the annotations control, the slices control, the layers control and the anatomical element all being displayed simultaneously; and
      at least a personalizing control which, when selected, is operable to receive control input for personalizing the visual image of the anatomical element to simulate a user's medical condition that is detected with the personalizing control;
   modifying the visual image in response to any control input received from any of the animation control, the annotations control, the slices control, the layers control, or the personalizing control; and
   presenting a specialist link which, when selected, displays contact information for one or more specialists associated with the anatomical element.

* * * * *